United States Patent
Goldstein et al.

[11] Patent Number: 5,899,937
[45] Date of Patent: May 4, 1999

[54] PULSATILE FLOW SYSTEM FOR DEVELOPING HEART VALVES

[75] Inventors: Steven Goldstein, Atlanta; Kirby S. Black, Acworth, both of Ga.

[73] Assignee: Cryolife, Inc., Kennesaw, Ga.

[21] Appl. No.: 08/812,303

[22] Filed: Mar. 5, 1997

[51] Int. Cl.⁶ .................................. A61F 2/24; A61F 2/76
[52] U.S. Cl. .............................................. 623/2; 73/865.6
[58] Field of Search .................... 623/1, 2, 3, 900, 623/901, 66; 73/37, 865.6

[56] References Cited

U.S. PATENT DOCUMENTS

| | | | |
|---|---|---|---|
| 3,638,536 | 2/1972 | Kleinwachter et al. | 623/26 |
| 3,758,237 | 9/1973 | Kachelhoffer | 623/3 |
| 3,860,968 | 1/1975 | Shapiro | 623/3 |
| 3,955,557 | 5/1976 | Takagi | 623/3 |
| 4,135,494 | 1/1979 | Stoner et al. | 623/1 |
| 5,163,955 | 11/1992 | Love et al. | 623/2 |
| 5,176,153 | 1/1993 | Eberhardt | 623/2 |

FOREIGN PATENT DOCUMENTS

| | | | |
|---|---|---|---|
| 1019-102 | 10/1977 | Canada | 623/3 |
| 92/05813 | 4/1992 | WIPO | 623/3 |

OTHER PUBLICATIONS

High–amplitude pulsatile pump in extracorporeal circulation with particular reference to hemodynamics; J. Thoracic Surg., pp. 798–808, Nov. 1963.

*Primary Examiner*—David J. Isabella
*Assistant Examiner*—Bruce E. Snow
*Attorney, Agent, or Firm*—Kenyon & Kenyon

[57] ABSTRACT

A closed, sterile pulsatile flow loop for studying tissue valves. The system provides both a tool to examine heart valve leaflet fibroblast function and differentiation as these are affected by mechanical loading, as well as an apparatus to provide heart valves seeded with suitable cells. The sterile pulsatile flow system provides a left heart duplicator, which exposes viable tissue valves to a dynamic flow environment imitating that of the aortic valve.

5 Claims, 3 Drawing Sheets

PULSATILE FLOW SYSTEM FOR DEVELOPING HEART VALVES

BACKGROUND OF THE INVENTION

The present invention is directed to the problem of providing heart valves for transplantation. More particularly, the present invention is directed to the problem of providing a flow system to assist in transforming a heart valve that is based on a xenograft into an autograft.

There is at present a shortage in the supply of heart valves available for transplantation. Indeed, since 1984, allograft heart valve transplantation in the United States has increased to over 2,400 grafts per year. Because of this increased demand, particularly for pediatric cases, the utilization of cryopreseved heart valves is not limited by the supply of donated human hearts. There remains a need to address this supply problem.

One approach, with which this application is concerned, is to turn to tissue engineering to create a graft. Such a graft would be immunologically acceptable to the recipient and have long-term durability that exceeds presently available homograft or chemically-fixed valves. Furthermore, a low incidence of failure due to leaflet calcification or stiffening would be expected. Based on the extracellular matrix remaining after decellularization of a porcine aortic valve, the remnant scaffold would be recolonized with autogenous fibroblasts recovered from the skin of the intended recipient. Ideally, the repopulating cells could functionally replace the native cells that were removed to enhance the immunologic acceptability of the graft.

Such living heart valves could be tailored to the intended recipient. These living heart valves could replace the diseased and damaged valves with one indistinguishable from the patient's own tissue. These valves would be self-repairing, capable of growth and response with the patient. Despite being the graft of choice for repair of congenital malformations, allograft valves do not grow necessitating additional surgeries to implant larger valves as the heart size increases.

SUMMARY OF THE INVENTION

The present invention is directed towards the development of such tissue grafts. This involves optimizing recellularization in a dynamic state. To accomplish this goal, there is provided a sterile, pulsatile flow loop system/bioreactor wherein a viable aortic tissue valve can be mounted and maintained in a dynamic flow under tissue culture conditions.

Since 1984 allograft heart valve transplantation in the United States has increased steadily to over 2,400 grafts yearly. Because of this increased demand, particularly for pediatric cases, the utilization of cryopreserved heart valves is now limited by the supply of donated human hearts. An objective of the present invention is to provide apparatus to help resolve this tissue valve supply problem through the continued development of a porcine valve substitute which is converted from a xenograft to an autograft. This can be accomplished by first ablating the antigenicity of the porcine valve through removal of native cells and soluble proteins in a manner consistent with valve structural integrity. The acellular, and presumably immunologically neutral, matrix can then be recolonized with recipient dermal fibroblasts under conditions which permit cellular attachment to the matrix, migration throughout the leaflet, and proliferation of the cells to a density and distribution typical of a natural valve. Dermal fibroblasts are chosen because of accessibility and rapid proliferation ex vivo, and because they synthesize types I and II collagens, the structural proteins whose continued renewal is considered important for the long-term durability of the tissue. In the prsent invention, a unique flow loop is provided, wherein intact, unfixed porcine valves can be subjected to pulsatile flow conditions reflecting those experienced by aortic heart valves in vivo while maintaining sterility and substrate exchange. The system then permits examination of the effects of flow rate, cycle frequency, and pressure non-depopulated porcine valves. This permits optimization of conditions for retention of cells reseeded onto the leaflet matrix, and investigation of how these physical forces affect the cellular activity of dermal fibroblasts (normally in a tension-regulated einvironment). These studies should permit development of production criteria for a tissue-engineered heart valve, while ensuring appropriate biosynthetic activity of the repopulating fibroblasts at time of implantation.

Flow systems have been used for in vitro hemodynamic studies and accelerated wear testing of devices of chemically fixed stented and non-stented heart valves. To date, none has been reported which can regulate flow rate, pulse frequency, pulse width, and back pressure within the physiologic range of each of these parameters for valves with living cells nor does once exist which can be operated under sterile conditions and for an extended period of time (>24 hr). A flow loop is provided which allows assessment of the impact of these parameters on the cellular functions of native and tissue engineered heart valves. The system can be validated with available glutaraldehyde-fixed stented aortic valves.

The system also is useful in helping to determine how flow dynamics modulates fibroblast function in viable porcine aortic valves. Despite the fact that heart valve leaflets must function in a dynamic flow environment, the activity of the important interstitial cells of these vital tissues is understood only from static cultures. The present system permits critical examination of the effects of critical flow parameters on the regulation of collagen and elastin gene expression and collagen and glycosaminoglycan biosynthesis.

A third goal of this system is that it will permit one to optimize the effects of flow on the repopulation of acellular porcine heart valve leaflets with human dermal fibroblasts; and examine how flow might be used to foster cell adhesion and cell function.

The understanding of the impact of flow on leaflet fibroblast metabolism obtained from the studies made possible by the system disclosed herein permits further progress toward the goal of developing the conditions necessary to make a living heart valve. Pulsatile flow can be used to modify both exogenous cell adhesion, migration, and activity so that we can achieve cell densities and function typical of native leaflet interstitial cells.

The ideal aortic heart valve replacement should be as similar as possible to the native valve. Homograft heart valves are an obvious choice. Unfortunately, donor tissues such as these are in short supply. The most readily available tissue valves(bioproshetics) are those from other species and are known as xenografts. Porcine valves are the most common xenograft. Unlike mechanical heart valves, bioprosthetics have a natural trileaflet structure and should have similar flow characteristics as human valves. To prevent immune responses to the cellular components of the valve, xenograft tissues are treated with chemical cross-linking agents such as glutaraldehyde. While this approach is successful in limiting acute rejection of these grafts, two detrimental consequences occur: first, leaflet flexibility is compromised, with bending stiffness of the leaflets markedly increased; second, glutaraldehyde fixation also increases the incidence and extent of leaflet and aortic conduit calcification, particularly in younger recipients. These factors combine to make bioprosthetic valves less durable and more prone to failure than natural valves.

Because of chemical fixation, current bioprosthetic grafts are composed of dead tissue. It is possible that the lack of biosynthesis of extracellular matrix proteins and mucopolysaccharides contributes to the failure of these valves. The goal of the tissue engineered aortic graft project is to develop a non-fixed tissue valve with a viable cellular component, phenotypically similar to that of a natural valve. If the native cells of the porcine tissue were removed, and if the leaflet was covered with human cells, the recipient's immune system would not detect the porcine tissue as foreign. By not chemically fixing the valve the leaflets would retain more of their natural flexibility and should thus function more efficiently. They might be less susceptible to calcification. Finally, the viable cells would provide for replacement of structural proteins damaged during leaflet motion, with resultant improved performance and durability of the valves.

Important questions remain as to adherence of repopulating cells of the leaflets and their functionality when exposed to the high stress environment of blood flow exiting the heart. Valve leaflets are exposed to several mechanical forces which may influence how well cells will grow and function on the leaflets. When the valve is closed during diastole, the valve must support systemic pressure, a normal stress that would directly affect the cells on the aortic side on the leaflets (lamina fibrosa). This stress may also be transmitted to cells within the tissue aligned to collagen fibers. The ventricular surface of the leaflets, on the other hand, experiences a fluid shear stress during systole when blood is ejected through the valve. Numerical simulations of flow through a stented valve indicate that this shear stress may exceed 130 dyne/$cm^2$ at peak systole. Bending stresses arise from the motion of the leaflets during the course of the cardiac cycle, and their effect on cell behavior is clearly seen in the elevated content of proteoglycans within the leaflet nearest the aortic wall. While several groups have studied these three types of stresses (1,2), particularly the normal and bending stresses, none has considered their effects on cellular function in a model which could isolate their influences separately.

During repopulation of a tissue matrix it is expected that fibroblasts initially will be deposited on the surface of the leaflets, but after static culture a fraction does recolonize the leaflet matrix. Those cells found at the surface would be exposed directly to flow in a vascular environment, while those within the collagenous matrix should be aligned with collagen fibers as in the native leaflet. The most extensive studies of the regulation of cellular activities in a flow environment have described responses of endothelial cells on the surfaces of vessels. In particular, these studies have modeled shear stress, the tangential frictional force acting in the direction of flow along a vessel's surface (3). The principal component of hemodynamic forces acting on the vessel wall is pressure-stretch which imparts compressive and tensile forces to both the surface cells as well as to the cells (smooth muscle, fibroblast) within the wall (4,5). Finally, both shear stress and hydrodynamic pressure effects are imposed in a cyclic manner as a consequence of the cardiac cycle; these phasic changes impose their own effect on cellular functions (6).

Though the cellular events altered by combinations of shear stress, pressure, and cycle frequency are numerous, of particular interest in considering how flow conditioning might affect the interactions of exogenous cells with a tissue matrix include adhesiveness of cells, proliferation rates, migration rates, and the ability of the cells to make extracellular matrix proteins. Among the adhesion proteins found on cell surfaces the strongest forces between cells and the extracellular matrix are mediated by the integrins (7). Each of these proteins has specificity for particular matrix proteins: collagen $a_1B_1$ and $a_2B_1$: fibronectin - $a_5B_1$; and a $B_1$; laminin - $a_6B_1$; vitronectin - $a_1B_3$; and the basement membrane receptor - $a_6B_4$. Synthesis of integrins and expression of their mRNAs is regulated in endothelial cells at even very low levels of shear stress 1.5 dyne/$cm^2$ of shear (8). Flow not only affects integrin synthesis but is also instrumental in reorganizing the localization of these proteins on the cell surface to increases resistance to detachment (9).

Fibroblasts within connective tissues are not exposed to shear stress, but they can be shown to respond to mechanical forces in their environment. These reactions appear to involve an interplay between the cells and their contained stress fibers, the extracellular matrix, and tensile forces developed by stretching or by application of pressure. Cardiac pressure overloading directly causes ventricular fibroblasts to proliferate and increase synthesis and deposition of types 1 and III collagens (10,11). Other cells are also pressure-responsive and much of the increased proteoglycan synthesis in cartilage remodeling is in response to this force (12,13). Fibroblasts obtained from the flexor tendons and cultured on elastic membranes are stimulated to proliferate, migrate, and increase collagen biosynthesis if subjected to cyclic tension changes; fibroblasts in wounds demonstrate traction-dependent changes in cell alignment (14–16).

Again, it is the direct action of the force which stimulates fibroblast proliferation and collagen synthesis. These functions are maximal in cells cultured in mechanically stressed substrata like anchored collagen gels (17,18). Relief of the stress is accompanied by progression of the cells to a quiescent state, with elevated expression of collagenase activity indicative of tissue remodeling rather than biosynthesis. Therefore, it should be expected that the ultimate localization of the cells either on the surface of, or within the matrix would significantly affect the result of repopulation of the acellular scaffold envisioned for those grafts. Indeed the strengthening of collagen gels used as wound models correlates with the contraction of these gels by the cells (19); similarly, the strengthening of ligament model systems correlates with applied traction on the collagen fibers. This elevates collagen cross-linking activity (20) and increase the diameter of newly synthesized collagen fibers (21), but only if the cells are embedded within the matrix.

These observations suggest that a bioreactor capable of physically preconditioning a living heart valve prior to implantation will be a necessary component of the process of manufacture of these tissue-engineered grafts. The application of optimal conditions of flow, pulsation rate, and pressure should provide an implant which displays physiologic levels of cellular activity, and provide a graft with extended durability and performance.

BRIEF DESCRIPTION OF THE FIGURES

For a more complete understanding of the invention, reference should be made to the figures, in which.

DETAILED DESCRIPTION

The applicants efforts in developing a tissue engineered heart valve prosthesis have been funded both by corporate funds and by two NIH Phase I SBIR grants.

1. 1R43 HL46607-01 Jul. 12, 1991–Dec. 12, 1991 Repopulation of Xenograft Heart Valves with Fibroblasts
2. 1R43 HIL53088-01 Aug. 1, 1994–Jan. 21, 1995 Xenograft Heart Valves: Biomechanics/Collagen Structure In the following summary, these grants are referred to as SBIR 1 or SBIR 2.

1. (SBIR 1) Porcine heart valves have been depopulated according to an autolytic procedure. Through the use of hypotonic buffers and nucleases, cells of cryopreserved porcine leaflets were made sensitive to lysosomal enzymes present in the native fibroblasts, which caused substantial removal of immunogenic components within 2 weeks of initiation of treatment. (Reduced inflammatory response has been verified in subdermal implant studies in rabbits and in sheep). This approach was taken, as the original use of cryopreservation and gamma irradiation in concert with repeated rapid freeze-thawings resulted in leaflet tissues clearly in disarray due to ice crystal formation, an effect not prevented by the addition of a variety of colloidal substances. Furthermore, use of detergents such as CHAPS<Triton X-100, or SDS were either found not to allow leaflet depopulation or to actually damage the tissue, shown by uniaxial biomechanical studies. In contrast, applicants final method retains leaflet ultimate tensile strength despite the likelihood of release of collagenase from the disrupted cells. This result is likely due to removal of divalent metal cations from the cell lysis solution and the consequential limitation of metalloproteinase activity.

The depopulation scheme does not remove the $\alpha$-gal-gal epitopes of pig tissues that appear to bind preexisting xenoantibodies. However, these can be removed by treatment of the intact valve leaflet with appropriate galactosidases. The epitopes can be removed from the conduit except in the endothelial lining of small vessels that invest the aortic wall.

Extensive uniaxial biomechanics studies have compared depopulated leaflets with fresh and cryopreserved tissues. The ultimate strength of the tissues are well preserved during depopulation at 37° C. Also, the extensibility of the leaflets either in radial or circumferential dimensions is not different from that of cryopreserved tissue; this is significant since the leaflets might otherwise have a propensity to prolapse.

Figure 1:
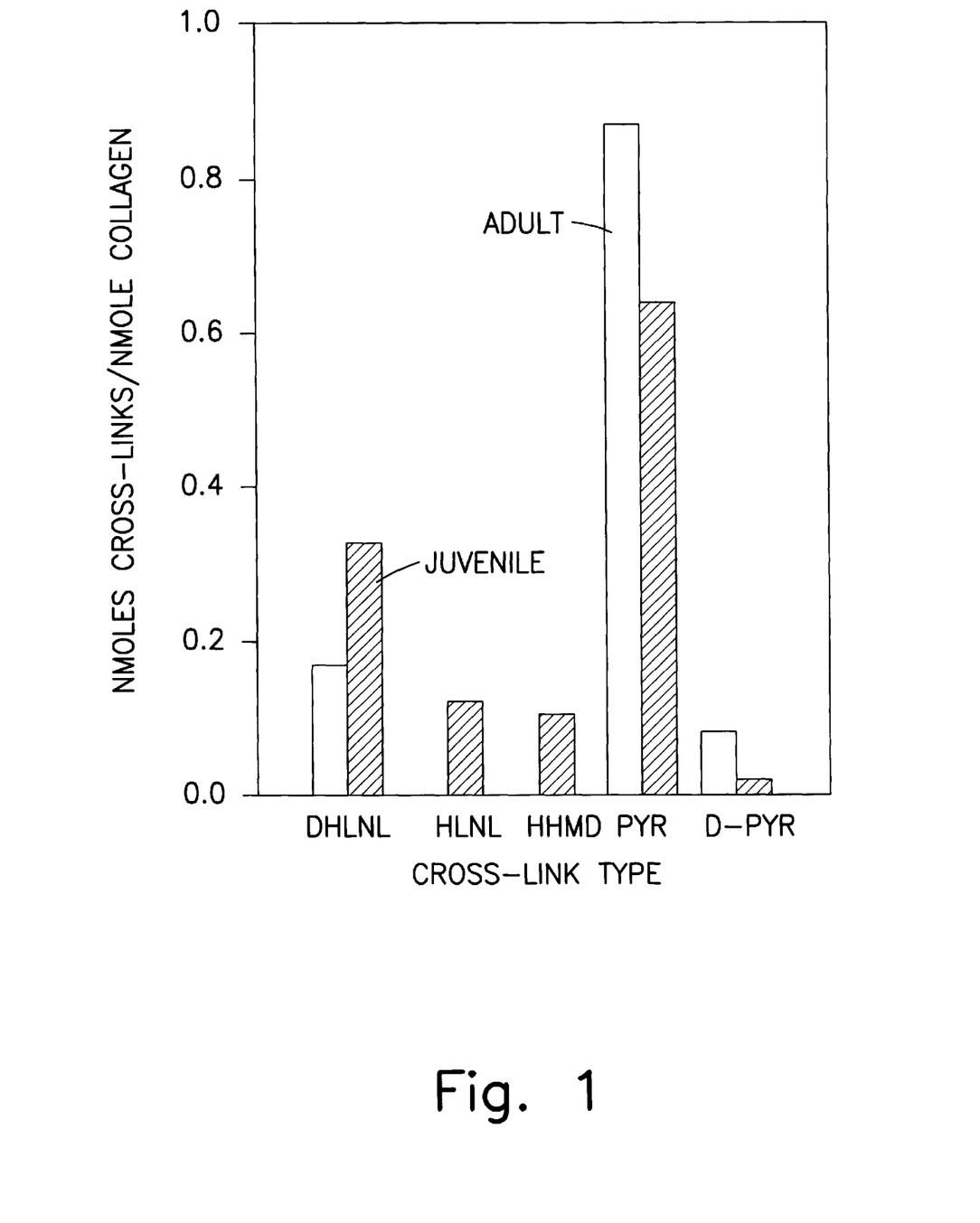
FIG. 1 is a graph showing reducible and non-reducible collagen cross-links in cryopreserved porcine aortic valve leaflets obtained from adult or juvenile hearts.

(SBIR 2) Valves obtained from young (<75 lbs) pigs were compared with those from adult (>250 lb) animals both for biomechanical properties as well as for collagen cross-links. Because of the large size of valves from older animals and the smaller size of the human recipient population which could benefit from a viable tissue valve, we compared the biomechanical properties of the leaflets of these valves. Ultimate load to failure, maximum stress, and high modulus (change in stress with change in strain) in the tissues from young animals were each about half the adult value in either circumferential or radial samples (Table 1). These differences appeared to be the result not of the extent of collagen crosslinking, but rather of the type of collagen crosslinks present. The leaflets were rich in non-reducible collagen crosslinks, a pattern more like that of load bearing cartilage than that of skin. The content of these crosslinks is lower in leaflets from young animals (FIG. 1).

TABLE 1

ULTIMATE TENSILE PROPERTIES OF AORTIC LEAFLETS
Comparison of Porcine vs. Human Aortic Heart Valve Leaflets

| Porcine | Adult | Juvenile | |
|---|---|---|---|
| Ultimate Load(g) | 1915 ± 622 | 834 ± 75 | p < .01 |
| Maximum stress (MPa) | 6.09 ± 0.62 | 3.54 ± 1.57 | p = .001 |
| High Modulus (MPa) | 28.5 ± 3.2 | 18.2 ± 1.7 | p < .001 |
| Human | Adult | Juvenile | |
| Ultimate Load (g) | 498 ± 93.5 | 350 ± 109 | |
| Maximum Stress (MPa) | 1.19 ± 0.2 | 1.72 ± 0.4 | |
| High Modulus (MPa) | 8.26 ± 1.43 | 9.88 ± 2.75 | |

FIG. 1 plots reducible and non-reducible collagen cross-links in cryopreserved porcine aortic valve leaflets obtained from adult or juvenile hearts. Tissues were processed as described above. Content of reducible cross-links was higher in juvenile tissues as compared to adult; levels of HLNL and HHMD were almost undetectable in the adult. In contrast, non-reducible cross-links, PYR and D-PYR were elevated in adult tissues relative to the juvenile. The content of reducible cross-links in this soft connective tissue structure is unusual and is more like the pattern of cross-links in mineralized collagenous tissues. This may reflect the mechanically active environment of the heart valve. Furthermore, the increase in non-reducible cross-links with age may indicate that the type of cross-link present is sensitive to the increase in systemic pressure that occurs during development. The collagen crosslinks do not change with the process of leaflet depopulation according to the currently used methods.

Leaflet and conduit repopulation have been attempted in tissues cut free from the valves; the repopulating cells have been sheep, rabbit, bovine, and human dermal fibroblasts. The selection of the dermal fibroblast as the repopulating cell type was chosen because: 1) it is accessible in a potential valve recipient; 2) biochemically, this cell synthesizes types I, III:, and V collagens in the same proportions (85:15:5) as are present in the heart valve leaflet (22)) and synthesizes proteoglycans (1,23) which are apparently important in reducing bending stress in the leaflets (2); and 3) endothelial cells do not seem to be necessary to prevent thrombus formation in cryopreserved aortic or pulmonary valves and they synthesize type IV collagen, the basement membrane collagen, which does not have a role as a structural protein.

The "best" repopulation has been with human dermal fibroblasts. Under conditions of static (no flow) culture, dermal fibroblasts will attach to the surface of the leaflets and, over a 2 week period, will migrate into the matrix of the tissue. The cell density of the repopulating cells does not reach that of either porcine or human aortic leaflets during this period; procedures to improve the degree of internal repopulation still have to be developed. These may include: 1) depopulation treatments that increase subsequent cellular access to the matrix; and 2) dynamic flow enhancement of cell proliferation and phenotypic expression after exposure to repopulating cells.

The cells that migrate into the tissue are functional. Autoradiographic analyses of tissues prelabeled with collagen precursor amino acids indicate that the repopulating cells are active in making this structural protein. Limited use of in situ hybridization also suggests that the repopulating cells are expressing type I collagen RNA.

Finite element, computational fluid dynamic (CFD) analysis of shear stress on the leaflet surface is of interest in this matter. The fundamental issue with engineering a living valve is to keep the repopulating cells adherent to the matrix; without this, the ability of the cells to function is unimportant. The shear stress on the leaflet surface is the least characterized mechanical force acting on the leaflet. To obtain an order of magnitude estimate of the shear stress on the leaflet surface, numerical simulations have been performed using a finite element solver, the Fluid Dynamics Analysis Package (FIDAP). In a finite element solution, the flow field is broken down into thousands of smaller regions called elements. The conservation equations that govern fluid flow are then solved in each of these elements to define a solution for the entire flow field. Although the eventual goal for the tissue engineered valve is a stentless design, flow through a stented aortic valve has been simulated. This geometry has a convergent flow filed that produces higher shear stresses on the leaflet surface, representing a worst case scenario for shear stress. Flow through the valves is modeled as flow through an axisymmetric nozzle rather than a full three-dimensional problem, which greatly reduces the computational time.

Figure 2:
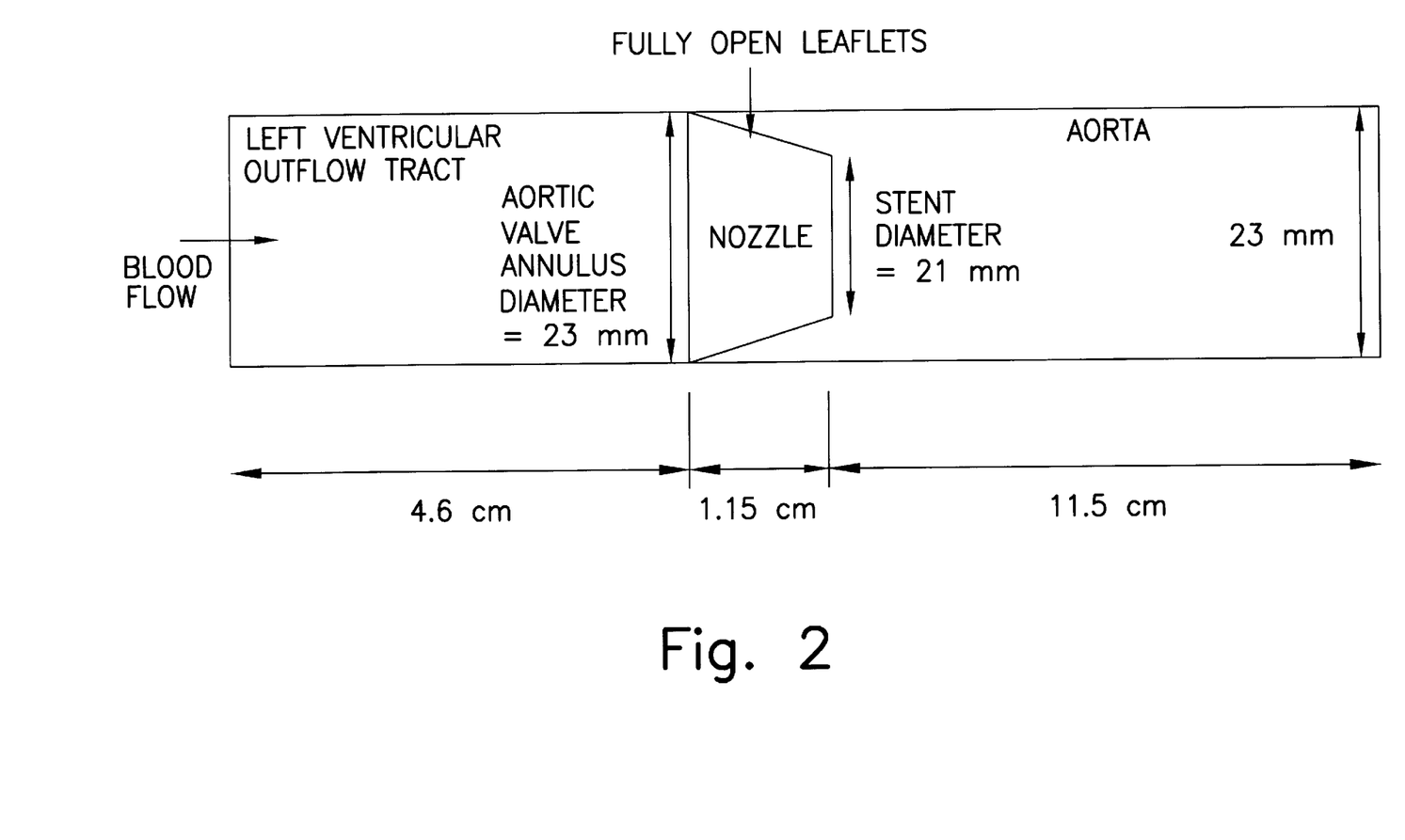
FIG. 2 is a schematic illustration of certain geometric parameters for simulations of shear stress on the leaflet surface. Flow through the aortic valve is modeled as flow through an axisymmetric nozzle. The leaflets are shown in the fully open position. The outflow from the valve can recirculate behind the leaflets.

A geometry that the invention models is shown in FIG. 2. Flow enters the valve from the left ventricular outflow tract (4.6 cm long). This inlet length allows FIDAP more freedom in converging to a solution but it is not long enough to allow flow to become fully developed before entering the valve. The diameter of the valve annulus is 23 mm, a typical valve size. To simulate a stented valve, the flow filed tapers as a nozzle over the next 1.15 cm to a typical stented valve outlet diameter of 21 mm. This differential of 2 mm approximates the difference observed in the subannular diameter and the supracoronary sinus aortic diameter. The leaflets are in a fill open position along the sides of the nozzle. The outflow from the valve enters a short (11.5 cm) segment of the aorta. This outlet length also helps the problem converge to a solution. The nozzle is contained within the aorta, so flow can recirculate behind the leaflets, which are 1 mm thick. The fluid properties are taken to be Newtonian with values modeling those of whole blood (density=1.05 g/cm$^3$; viscosity=3.5 cP). Although whole blood is a non-Newtonian fluid, it behaves as a Newtonian fluid at the high flow conditions seen at the aortic valve.

Four different inlet flow conditions were simulated. The first two cases are simple laminar flows at a cardiac output of 5 L/min, entering the model as a flat or parabolic profile with a mean velocity of 20 cm/s. We also considered a turbulent flow at 30 L/min (120 cm/s) to simulate the flow rate at peak systole at a cardiac output of 7.5 L/min. The fourth case is a pulsatile flow. The cardiac cycle is approximated as a half sine wave at a normal resting frequency of 60 bpm. The systolic (ejection) phase occurs over the first half of the cycle, with a peak velocity of 120 cm/s. Although we have not yet done so, this waveform could be varied in frequency, peak velocity, or systolic duration. One problem with modeling the cardiac cycle is deciding whether the flow is laminar or turbulent. Flow is initially laminar, but becomes turbulent near peak systole, and during the deceleration phase. However, in FIDAP and most other simulation packages, the user must choose between the two flow regimes and apply that choice to the entire flow cycle. Since higher shear stresses are expected near peak systole, we solved this problem as a turbulent flow to model peak systolic conditions more closely. Turbulent solutions used the k-6 model with a separate algorithm to capture near-wall behavior.

As flow converges into the nozzle (through the valve), its mean velocity must increase by conservation of mass. While the centerline velocity increases, the velocity at the wall must remain at zero by no slip conditions. As a result, steeper velocity gradients develop near the wall, causing higher shear stresses on the leaflet surface. The shear stress should reach a maximum at the nozzle outlet (leaflet tips), the point of maximum convergence. In pulsatile flow, the highest shear stresses should be observed near peak systole, when flow through the nozzle is accelerating in time as well as accelerating due to the converging geometry. Recirculation should be apparent downstream of the nozzle outlet. These patterns have been observed in all of our simulations. The maximum shear stresses observed are listed in Table 2. The highest shear stresses were observed on the nozzle tip and reached a maximum of 135 dyne/cm$^2$.

TABLE 2

Summary of shear stresses on the leaflet surface observed in simulations of flow through a stented valve

| Inlet Condition | Shear Stress (dyne/cm$^2$) |
|---|---|
| Flat, laminar profile at 20 cm/s | 12 |
| Parabolic, laminar profile with mean of 20 cm/2 | 8 |
| Flat, turbulent profile at 120 cm/s | 124 |
| Pulsatile flow with peak of 120 cm/s | 135 |

It is difficult to relate this shear stress estimate to behavior on the cell monolayer. Early attempts to determine the strength of cell adhesion involved increasing the shear stress until the cells sheared away. Aortic endothelial cells, normally exposed to shear stress of 15 dyne/cm$^2$ is reached (25). Whether the cell will shear away from the leaflet surface depends upon the number and strength of the bonds that anchor the cell to the surface. Most cell adhesion research has focused on the cells of the immune system, such as leukocytes and neutrophils, which can roll along the endothelium to find and adhere at sites of inflammation. Examining neutrophil adhesion to the endothelium, Springer (19) has found that the strength of one characteristic bond is 110 pN; a similar value was found by Evans, et al. (26) with agglutinated membrane capsules. Several such bonds are required to cause adherence. For example, micropipette experiments demonstrated that the force required to separate a sarcoma cell from an endothelial cell or fibroblast is on the order of 100 μdyne (27). Hammer and Lauffenberger (28) developed a mathematical model of the adhesion of isolated blood-borne cells to a cell surface to predict conditions favorable to cause adherence. For example, micropipette experiments demonstrated that the force required to separate a sarcoma cell from an endothelial cell or fibroblast is on the order of 100 μdyne (27). Hammer and Lauffenberger (28) developed a mathematical model of the adhesion of isolated blood-borne cells to a cell surface to predict conditions favorable to cell adhesion. If the fluid shear stress is strong enough to prevent or disrupt the formation of these bonds, the cell will not adhere. However, the adhesion of a monolayer of cells bound to their extracellular matrix has not been modeled. The adhesion molecules typically involve in these two processes are different. Immune cells typically begin attachment to the endothelium through selectins, while cell adherence to the extracellular matrix is generally due to integrins (25).

The shear stress estimate can be refined by the addition of several small but important details. The left ventricular outflow tract (LVOT) is not straight but tapers slightly proximal to the aortic valve. More importantly, the leaflets are not perfectly straight in vivo, as depicted in this model. They bend during the cardiac cycle in response to changing flow conditions. A simple nozzle predicts that the maximum stress will occur at the leaflet tips, but a curved leaflet may have larger stresses near the plane of the curvature. One limitation of FIDAP, however, is that the solid boundaries cannot move, so fully mobile leaflets cannot be simulated. Instead, we will try to model various stages of the opening phase of the systole by a pseudo-steady state approach, using reduced flow rates, with leaflets having varying degrees of curvature, and more convergent outflow (orifice) diameters.

As noted above, there is a need, which is addressed herein, to develop a sterile, pulsatile flow loop systemibioreactor wherein a viable aortic tissue valve can be mounted and maintained in a dynamic flow under tissue culture conditions.

Despite the fact that cells in heart valve leaflets operate in a mechanically dynamic environment, most studies of leaflet cell metabolism have been carried out in static culture. In the few exceptions to such observations, leaflet energy charge and protein labeling having been examined during the period after death as the valves reprogram from a dynamic environment to a static condition. Both phosphorylated adenylates (29,30) and protein biosynthesis (31,32) were observed to decline in logarithmic fashion over a period of days despite provision of standard cell culture conditions; leaflet cellular viability declined during this period as well. The reasons why leaflet fibroblasts could not be maintained within the leaflet matrix for longer periods are not clear, as primary cultures of fibroblasts made from explants of such tissues can be cultured as monolayers for many doublings and passages before undergoing senescence (Goldstein, unpublished observations). One significant difference may be the absence of key physical input since valves in static culture are not subjected to usual dynamic flow forces while fibroblasts in monolayer culture are in physical tension with the substrate. A bioreactor is presented to study effects of physical inputs to heart valve leaflet biochemical functions; an In vitro flow loop for simulating aortic valve environment.

Figure 3:
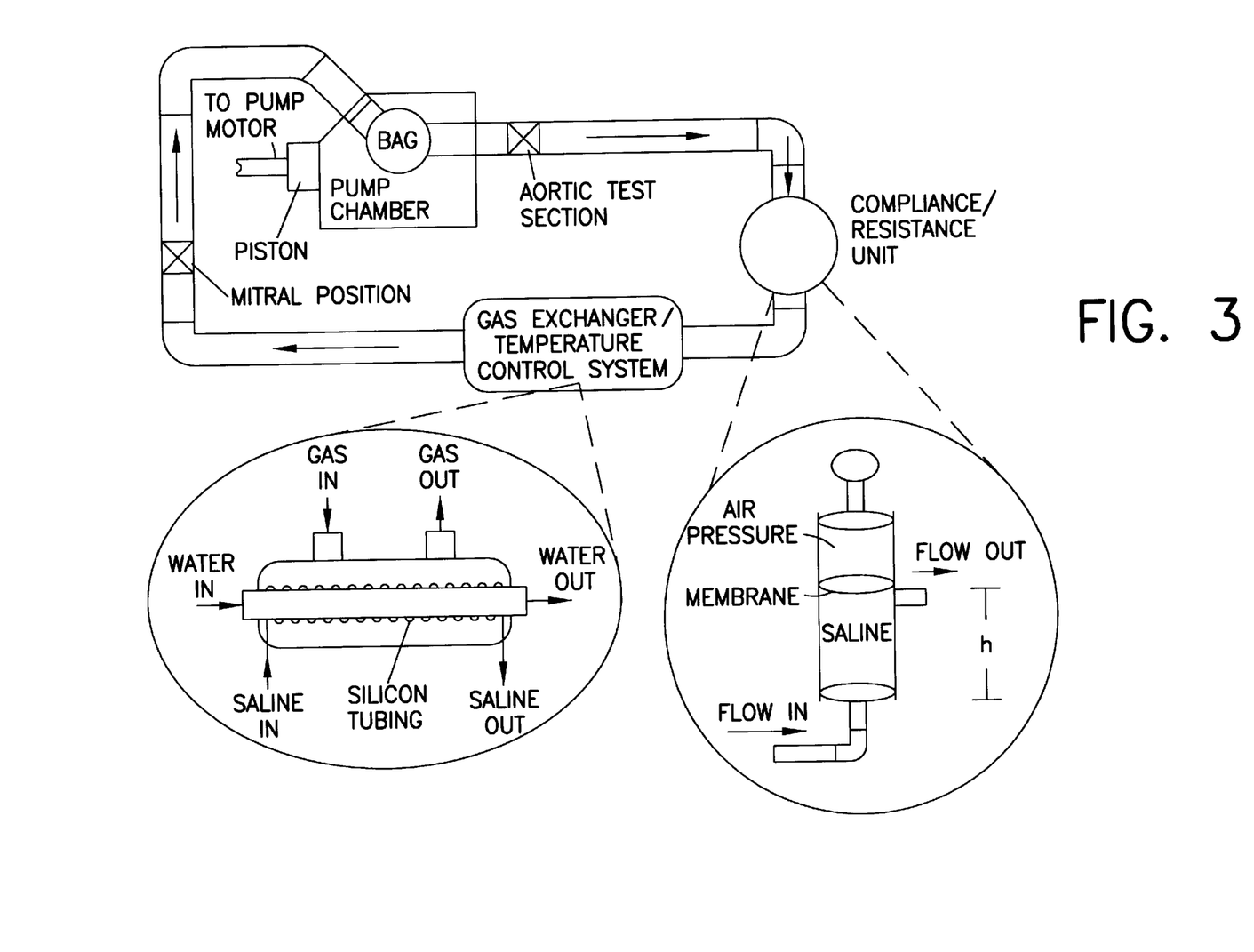
FIG. 3 schematically illustrates an in vitro flow loop for analyzing aortic valve function. The left ventricular model is shown, and the inset figures illustrate the compliance/resistance element and the gas exchange/temperature control unit.

The first phase is to study the cellular activity of a normal, living porcine aortic valve under physiologic conditions in an in vitro flow loop. The in vitro flow loop models the left heart and consists of a mechanical mitral valve, a bladder simulating the left ventricle, a test section with aortic valve samples mounted in parallel, a downstream compliance and resistance element, an oxygenator, and a heat exchanger (FIG. 3). A piston pump (Vivitro Model SPS 3891) can be used to drive the pulsatile flow, since its motion can be programmed with a waveform generator (Vivitro Model WG 5891), allowing the flow waveform to be changed easily. The left ventricle is approximated by a flexible rubber bladder mounter inside of a Lexan chamber filled with water. The piston can displace the water; this in turn will squeeze the flexible bladder and propel the blood analog fluid out through the aortic valve test section. In this way the piston pump controls flow through the system without actually contacting the sterile fluid in the loop. The piston motion will be programmed to produce a flow that simulates the cardiac cycle as the half sine wave previously described, but with variable frequency from 60–120 bpm and a cardiac output of 2–7.5 L/min. This pulsatile flow will be applied continuously for the duration of the experiments.

Porcine aortic valves are obtained at slaughter. The porcine root are slid inside the simulated aorta made from a silicone elastomer. The inflow and outflow edges of the valve are attached to the aortic model by a continuous line of blanket stitching using 5/0 and 4/0 suture, respectively. This prevents the leaflets from prolapsing back into the left ventricle during diastole. Both lines of stitching are sealed with a silastic medical adhesive to prevent leakage. We have used these techniques previously in flow studies with nonstented, glutaraldehyde-fixed porcine aortic valves (33). Since experiments may last for a week or more, it would be advantageous to test valves in parallel. This can be accomplished by splitting the inflow into three separate paths, each with its own aortic valve assembly. Gate valves will separate each path, allowing one line to be isolated from the others should problems develop. We have calculated the displacement capacity of the piston and the volume of the flow loop and have estimated that it is possible to study three valves simultaneously.

A mechanical prosthetic valve is needed in the mitral position to keep flow going in the proper direction. Either a tilting disc valve or a bileaflet valve will be used. An adjustable resistance and compliance element (FIG. 3) is placed downstream to simulate the peripheral resistance of the circulation. Compliance will be provided by allowing the fluid to collect in a Lexan tank and to push against a flexible membrane. The membrane serves to separate the sterile fluid from the unfiltered air. The pressure in the air space above the membrane can be varied to adjust the compliance through a physiologic range of values. Westerhof et al. (34) found that a compliant volume of roughly 900 $cm^3$ should adequately duplicate the physiologic capacitance of 0.008 $cm^3$/mm Hg. Resistance is provided by raising this tank above the rest of the loop. This creates a pressure head against which the fluid must flow to enter the tank. Additional resistance could be provided by clamping down on a flexible tube included downstream. These measures should adequately duplicate the physiologic resistance of roughly 1200 g $cm^{-4}$ $s^1$ (34). The downstream compliance and resistance will be adjusted to provide physiologic aortic pressures of 120 mm Hg systolic and 80 mm Hg diastolic, duplicating the back pressure on the aortic valve.

The fluid used must contain nutrients to support the metabolism of the living tissue of the hear valve. Whole blood is difficult to use experimentally because of its clotting properties, so a tissue culture medium will be used. Plasma expanders, such as hydroethyl starch, polyethylene glycols, or polyvinylpyrrolidone will be added to increase the viscosity of the fluid to that of blood. Oncotic pressure will be provided by proteins in fetal bovine serum used as a source of growth factors. To avoid introducing potentially harmful impurities into the system, all materials that may contact the fluid (tubing, fittings, probes) must be sterilized. The tubing will be made from a grade of Lexan (GR series, General Electric) which is sterilizable by ethylene oxide gassing. All flow loop components will be sterilized with ethylene oxide gas; local vendors will provide rapid turn-around time between successive valve mountings. Medical grade tubing connectors will be used. The flow loop will be constructed from transparent materials so that its internal cleanliness may be visually inspected throughout the course of the experiments. The sterility of the fluid will be analyzed daily by withdrawing a small sample from each parallel flow path and checking it for contaminants.

Although nutrient replacement should not be required over short-term experiments (1–2 weeks), gas exchange will be necessary to maintain oxygen tension and regulate bicarbonate levels. The temperature of the fluid must also be maintained at 37° C. Oxygenation and temperature control will occur in a specially designed unit (FIG. 3). In this unit termostated water flows through the glass core tube, while medium flows through a gas-permeable silicone tube coiled around the core. A feedback control loop could be employed to adjust the temperature of the incoming water to maintain the proper medium temperature. A Lexan tube encloses the glass core. A $CO_2$/air mixture will be supplied to the annular space, allowing oxygen to diffuse into the silicone tubing and waste gases to diffuse out. Spent gas can be vented from the annular space.

Due to the length of the experiments, conditions will not be monitored continuously. However, parameters such as temperature, flow rate, pressure, and pH must be checked periodically to evaluate the performance of the flow loop and contained heart valve. These conditions will be monitored every 6 hours using a sophisticated on-line, 12-channel data collection, display, and analysis system (CardioMed, Model CM-4008, Norway). It can display up to 6 signals in real time, including differences between two waveforms (such as pressure drop). Time derivatives of any waveform can be displayed, and integration can be performed over a specified time interval (for example, stroke volume can be found by integrating the flow waveform over one cycle). Each parallel path will be equipped with an ultrasonic flow probe (Transonics Systems, Model 24N) distal to the aortic valve, two pressure taps, and a port for withdrawing fluid samples. Absolute pressure transducers (Baxter, Uniflow) will be located both upstream and downstream of the valve to allow both the aortic pressure and the pressure drop across the valve to be recorded. The pressure transducers will be interfaced to a bridge amplifier. Flow and pressure waveforms measured in each path will be compared to verify that each valve experienced similar flow conditions. High-speed videography (Kodak EktaPro System) will be used to monitor the opening and closing characteristics of the valve. This will necessitate a right angle outflow window on the heart valve mount; this position of the video window will be preferable to imposing a non-inline flow path on the inflow side of the test valve.

To characterize the flow field near the aortic valve, the system should be amenable to noninvasive flow analysis by color Doppler flow mapping (CDFM), spectral Doppler analysis, or laser Doppler anemometry (LDA) All three of these techniques are available for this system. CDFM and spectral Doppler analysis can be performed on an ultrasound machine (Sonolayar SSA-270A, Toshiba). CDFM color codes the velocity field through the valve, giving a sense of the overall flow field. Spectral analysis can be done with either continuous wave (CW) or pulsed wave (PW). CW measures the velocity distribution along a specified lim while PW measures the velocity at a particular region of interest. Thus CW could be used to measure the peak velocity through the valve at the centerline, while PW could be used to estimate the fluid velocity at the leaflet tips. Three-component LDA (Aerometrics) could provide a more accurate estimate of the velocity at the tips since it has a smaller interrogation volume (0.3 mm in length) than is possible with PW. This estimate could be used to calculate the shear stress on the leaflet surface, providing a potential validation of our numerical simulations (see Preliminary Results). Each of these techniques—CDFM (35), spectral Doppler analysis (33), and LDA (36,37)—have been used extensively in Dr. Yoganathan's laboratory for the past 15 years.

Before experiments begin with fresh porcine valves, the overall performance of the loop should first be tested to verify that the desired flow conditions can be achieved in a sterile environment. These initial tests require two phases. First flow conditions should be verified. These tests would not need to be run under sterile conditions, allowing any necessary modifications to be made to achieve the correct conditions. At this stage, mechanical valves could be used in the aortic and mitral positions, and the fluid should still simulate the viscosity of the tissue culture medium. Once the flow conditions are verified, the flow loop materials will be sterilized and tested again with stented bioprosthetic valves in place. This will serve to test the ability to maintain sterile flow conditions over a short (24 hr) period of time. Once these conditions have been verified, the materials will be realized again before proceeding with the fresh porcine valve experiments described below.

A further aim of is to determine how flow dynamics modulates fibroblast function in viable porcine aortic valves. At least three types of cellular functions have been associated with mechanical regulation of connective tissue strength: collagen biosynthesis vs. degradation, i.e., net collagen accumulation; collagen fiber diameter, and collagen cross-link density including the nature of the cross-links formed. These functions may be directly responsive to mechanical forces, but may also respond seconds to changes in the amount and nature of extracellular matrix factors such as proteoglycans produced by fibroblasts or to autocrine or paracrine factors. Produced by fibroblasts or neighboring cells. Proteoglycans appear to have specific influences on collagen deposition and structure (38). Furthermore, the distribution of proteoglycans is topographically restricted in native heart valve leaflets (1,2,39); their density is greatest in the hinge region Of the leaflet (sites nearest areas of extreme bending moment near the aortic wall) as opposed to the region of the leaflet proximal to the coaptive areas where tensile loads are noximal.

Besides the differential expression of extracellular matrix biosynthetic activity, physical stress also appears to confer a contractile cell-like phenotype to the fibroblasts of the leaflets (40). After collagenase digestion of the leaflets, the need cells grew as monolayer cultures morphologically similar to typical dermal fibroblasts. They contained vimentin filaments, and expressed fibronectin, chondroitin sulfate, and prolyl-4-hydroxylase activity typical of fibroblasts. Specialized differentiation of these cells was indicated, however, by the presence of ($\alpha$-smooth muscle actin fibers.

A connection between the stresses experienced by heart valve leaflets and their biosynthetic activities was postulated by Schneider and Deck (1). Through autoradiographic analysis using precursors specific to protein or glycosaminoglycans, they found that cells actively engaged in the biosyntheses of collagen were more likely to be found in regions of the leaflet subjected to the greatest amount of loading forces. (In vivo measurements in dogs allowed measurement of bending stresses and pressure and membrane stresses in the hinge region of the leaflets (2)). In contrast, sulfate accumulation (presumably representing sulfated glycosaminoglycans) was greatest near the hinge region between the leaflet and adjacent aortic conduits These results confirmed the earlier report of Torii, et al. (41) who postulated that glycosaminoglycan synthesis in leaflets is inversely proportional to imposed pressure.

Direct demonstration of the effects of pressure on leaflet metabolism was obtained from studies of heart valves from spontaneously hypertensive rate (10). Proliferation index measures, collagen labeling, and types I and III collagen gene expression were all increased after mean arterial pressure was elevated by 25% in the affected animals.

The effects of the differing forces of pressure and bending were apparent in presence of myofibroblast like cells in the leaflets (42). These cells appeared more numerous in the distal portions of the leaflets and were distinguished phenotypically by their content of α-smooth muscle action. After explant culture, these cells retained ability to contract with application of a variety of pharmacologic agents (40), suggesting a possible role for these cells in leaflet motion. Again, physical forces may be important not only as a regulator of fibroblast function, but also of cellular differentiation.

Mechanical loading (tension) affects dermal fibroblast replication and collagen production independently of autocrine, paracrine, or endocrine factors (14). Pressure overloading of the heart causes cardiac hypertrophy which involves, in addition to cardiomyocyte hypertrophy, the replication, and elevated synthesis of collagen by cardiac myofibroblasts (10,11). While collagen synthesis appears to require more than 24 hr of increased tension to be upregulated in fibroblasts, the transduction of physical forces into other cellular responses may vary according to cell type, physical force involved and the end-point measurement. For example, there is a hierarchy of appearance and disappearance of effects of flow on endothelial cells (7) in which shear stress requires from 6 to 48 hours to produce alterations in adhesion molecule appearance on the cells. While short times may be required to provide maximal rates of expression of integrins, reorganization of cells within the extracellular matrix may take longer as is shown by the time it takes randomly arrayed endothelial cells to reorient to minimize shear stress once flow has begun (43).

In light of these observations, we will utilize the system described above to expose fresh (unfixed, viable) porcine aortic heart valves to normal blood flow conditions; frequency will be 70 bpm with a diastolic pressure of 70 mg Hg and a flow rate of 5 L/min. Collagen biosynthesis (total and differential based on type I and type III collagens), type I, III, and IV collagen RNAs and elastin mRNA, and glycosaminoglycan synthesis will be examined after continuous treatment for up to 5 days. The distribution of the cells engaged in the synthesis of collagen versus glycosaminoglycans will be assessed by autoradiographic analysis of lengthwise cross-sections of leaflets. Other samples will be tested for ultimate tensile strength. The influence of elevated rate (120 bpm), elevated pressure (120 mm Hg), and elevated flow rates (7.5 L/min) on these measures of leaflet metabolism will then be inspected. It is likely that most of the metabolic changes which might occur in response to changes in pulsatile flow will occur within 24–48 hr (v.s.).

Finally, leaflet specimens from each of these conditions will be immunostained with antibodies selected from those listed in Table 3. One aim is to examine the effects of flow dynamics on the adhesion and proliferation of dermal fibroblasts reseeded onto an acellullar aortic valve matrix. Pulsatile flow may modulate the expression of critical proteins involved in fibroblast adherence to the collagenous matrix of the leaflet. These immunostaining studies will provide the first data on the interaction of flow and fibroblast integrin expression and cell distribution. This will provide the tools to optimize porcine matrix preconditioning and bioreactor flow conditions to produce a "normal" living heart valve.

TABLE 3

IMMUNOHISTOCHEMISTRY REAGENTS

| TARGET | EPITOPE LOCATION | ANTIBODY or LECTIN | SOURCE |
| --- | --- | --- | --- |
| MHC Class I Antigen | Mammalian Cell Membranes | H58A | VMRD, Inc. Pullman, WA |
| MHC Class II Antigen | Human Cell Membranes | H34A | VMRD |
| MHC Class II Antigen | Porcine Cell Membranes | MSA3 | VMRD |
| Carboxyl terminal Domain of Type I Procollagen | Fibroblast Cytoplasm | Anti-pC | John Hopkins University |
| Fibroblast Antigen | Mammalian Cells | RCV508C1 | Washington State University Monoclonal Antibody Center (Dr. Bill Davis) |
| α-Smooth Muscle Actin | Smooth Muscle Phenotype | NCL-SMA | NOVO Castra |
| Desmin | Contractile Cells | Clone DIG10VL2 | Sigma |
| Integrin $\alpha_2\beta_1$ | Collagen Receptor | | Chemicon International |
| Integrin $\alpha_2\beta_1$ | Collagen, Laminin Receptor | M0608 | DAKO |

A further aim is to optimize the effects of flow on the repopulation of acellular porcine heart valve leaflets with human dermal fibroblasts; examine how flow might be used to foster cell adhesion and cell function.

The tissue engineering concept guiding the development of this heart valve is an attempt to mimic, as closely as possible the distribution of cells and the expression of cell activities found in a native leaflet that are considered important for long-term leaflet durability. We have been able to remove the porcine cells from the heart valves without reducing the strength of the tissue. We have also replaced the cells in the porcine heart valve with human dermal fibroblasts demonstrating that the leaflets can be recellularized. The next phase of this project is to optimize the recellularization process in a dynamic system.

Background—Cell adhesion in the flow environment—Endothelial cell seeding of small caliber vascular graft surfaces has been attempted to reduce the natural thrombogenicity of both synthetic and natural conduits used as bypass grafts. When cells were seeded immediately before implantation of a graft into a high flow environment (44–46), or even if they were cultured with the graft material under static, tissue culture conditions (47), poor endothelial cell retention resulted and clot formation due to the graft remained accelerated (47). Duration of graft patency was short. However, when endothelial cell seeded grafts were exposed to graded increases in shear stress over time, and then exposed to arterial shear stress (25 dyne/cm$^2$), short-term cell adhesion and prevention of clot formation were improved (47). Similar improvements in graft patency resulted when endothelial cell adhesion was supplemented with an exogenous biocompatible fixative (fibrin adhesive) and the cells were allowed to maximize intercellular bonding *48). The linkage between shear stress and endothelial cell adhesion molecule expression was clear as physiologically relevant levels of shear stress (>2.5 dyne/cm$^2$) upregulated ICAM-1 gene expression and insertion into cell membranes (49).

Fibroblasts seeded onto an acellular matrix would experience forces different from those found within the leaflet matrix. Stress is force per unit area. Blood pressure acts normal to the surface and creates a compressive stress. Friction force of flowing blood generates a shear stress acting tangentially tot he cell surface. Distention of the substrate due to a pressure pulse transmits tensile stress to cells through the contacts with the extracellular matrix. Cell deformation as a response is expressed as stain and depends on the mechanical and structural properties of the cell. Cells within the matrix will be exposed to tensile strain (stretch), the change of length per unit length. Torsional stresses may be imposed across the cell if it behaves as a solid.

While it is clear that fibroblasts have a tensional force sensor mechanism, the question remains whether shear stress or pressure can be utilized to optimize their adhesiveness to a mobile substratum such as a leaflet and increase the efficiency of repopulation. To examine this, valves will first be seeded with dermal fibroblasts under static culture conditions. After a 3 hr attachment phase, the valves will be placed in the flow loop which will be utilized to slowly increase flow rate (starting at <10 ml/min); to this we will add a cycling flow parameter to induce leaflet flexion. In another paradigm, a constant pressure field will be applied, again starting at low levels and ultimately ramping up to normal diastolic levels. The studies of pressure field will be applied, again starting at low levels and ultimately ramping up to normal diastolic levels. The studies of pressure can be carried out without the flow loop as the initial studies will examine this force independent of flow rate or cycle frequency. In each case, leaflet integrin expression will be compared to valves incubated in static culture for the same time as the dynamically loaded valve leaflets.

Is likely that cellmigration will be affected due to the tension on the collagen fibers produced by elevated force levels. To assess cellular distribution, valves will be conditioned at reduced or elevated (compared to normal) flow rate, frequency, and pressure and leaflets exposed to these treatment conditions will be radiolabeled with protein and proteoglycan precursors and analyzed by autoradiography to provide data on distribution and activity of viable cells within the leaflet matrix. Samples will also be submitted for in situ hybridization to examine distribution of cells specifically expressing types I, III, and IV collagen mRNAs and elastin mRNA.

MATERIALS AND METHODS a. Materials

Pig Tissues—Approximately 20 pig hearts can be obtained weekly at slaughter from AVCO Meats, Gadsden, Ala.: this facility is 2 hours from CryoLife, Inc. These hearts are from adult animals weighting 90–300 kg. Hearts will be rinsed at the slaughterhouse in sterile saline and transported on wet ice in Dulbecco's modified Eagle's medium. At CryoLife, Inc., the aortic valves will be dissected free in a class 100 clean room and incubated in an antibacterial/antimycotic solution at 37° C. for 24 hr. The treated valves are washed in antibiotic-free DMEM and transferred to 4° C. DMEM containing 10% DMSO and 10% fetal bovine serum (Gibco/BRL) and placed in heat-sealable pouches. Finally, the valves will be cryopreserved in a controlled rate freezer (CryMed) using liquid nitrogen to reduce temperature at 1° C./min to–80° C. Then, they will be transferred to liquid nitrogen (–196° C.) until use. Pig leaflets from cryopreserved tissues have metabolic heat production rates up to 90% of those of fresh tissues (S. Goldstein, unpublished results). Prior to use, the pouches containing the frozen valves will be plunged into 37° C. water to rapidly thaw the tissue to prevent formation of ice crystals and consequent structural damage. DMSO will be removed with sequential washes in sterile lactate Ringer's solution containing 5% dextrose.

Human Dermal Fibroblasts—Upper thigh skin will be obtained from cadaver material after receiving appropriate research consent. Fibroblasts will be grown by culture of~1 mm$^3$ explants in 35 mm culture plates placed in a humidified, 37° C., 5% $CO_2$ environment. Fibroblast outgrowth can be achieved within 2 weeks. The cells will then be passaged by trypsinization, washed, and plated in 75 cm$^2$ culture flasks. The cells will be fed twice weekly with DMEM containing 10% fetal bovine serum. The cells will be passaged at confluence and utilized between passages 4 and 9.

b. Methods

1. Microscopic Methods a) Light microscopy-histology and staining procedures; immunohistochemistry Paraffin-embedded or frozen sections will be stained with hematoxylin and eosin for routine screening of tissues. Cell counting will be performed with the aid of a micrometer eye piece at 100× magnification. Ten regions will be chosen randomly along the length of each hematoxylin- and eosin-stained cross-section of leaflet for counting of intact cells and for evidence of pycnosis. Function and species-specific antibodies will be used to assess depopulation (porcine MHC class II and fibroblast antigen). Reseeded human cells will be detected with MHC Class II antigen. Type I procollagen will be used to monitor fibroblast function while smooth muscle actin and desmin will be monitored to detect differentiation to a myofibroblast phenotype. Collagen dependent cellular ligands will be detected with antibodies to integrins $\alpha_2\beta_1$ and $\alpha_3\beta_1$. Identification of these antibodies will employ a system of biotinylated secondary antibodies. In addition, avidin/biotin blocking and Vectastain Elite ABC kits (Vector) with immunoperoxidase staining and a Harris hematoxylin counterstain will be employed. Differentiation of viable versus non-viable cells will be provided by fluorescence microcopy of sections stained simultaneously with nucleic acid probes that fluoresce different colors based on permeation into live or dead cells (Molecular Probes, Eugene, Oreg.).

b) Electron Microscopy

Selected leaflet sections will be analyzed by electron microscopy to define effects of depopulation and flow conditioning on collagen fibril integrity. Samples for transmission electron microscopy will be post-fixed in 2% osmium for 1 hr and dehydrated through an alcohol series, followed by Epon embedding. The specimens will be cut in a-2 $\mu$m sections and stained with toluidine blue. Based on this staining, representative areas will be selected and ultra thin sections made and stained with a saturated solution of uranyl acetate in water and lead citrate for positive staining, or with phosphotungstic acid at neutral pH for negative staining. Leaflet surfaces will be examined by scanning electron microscopy. Samples for SEM will be post-fixed in 2% osmium in phosphate buffered saline for a minimum of 4 hr, washed with PBS, treated with thiocarbohydrazide for 1 hr and then reexposed to osmium. The sections will be studied with an electron microscope at the Yerkes primate Center (Emory University) and examined qualitively by Rob Apkarian.

c) Autoradiography

After exposure to variations of pulsatile flow and pressure conditioning (v.s.), selected leaflets will be dissected and metabolically labeled in the presence of $^3$H-proline or $^3$H-sulfate to label proteins and glycosaminoglycans, respectively. After labeling, the tissues will be treated with 10% trichloroacetic acid. then they will be extensively washed to remove unincorporated label and fixed in 10% neutral buffered formalin. The fixed tissue will be frozen in OCT and cut in 6 μm sections. the sections will be mounted on chrome alum-coated positive-charged glass slides. Each tissue block will be cut into three pieces per slid, with three test slides and three experimental slides allowing for optimization of exposure time. the embedding medium (OCT) is then removed and the tissue defatted with successive dilutions of ethanol in water. A photographic emulsion (Kodak NTB2) will be applied to the slides, and development will proceed at 4° C. At selected times, the exposed emulsion will be developed (d-19 developer) and fixed (Kodak Polymax T fixer), and the tissues counterstained with Harris hematoxylin and eosin. the distribution of cells active in metabolism of the particular precursor will be determined microscopically. video imaging software (Simple, C-Imaging, Pittsburgh, Pa.) will be used to automatically map developed grains as indicators of cellular activity.

2. Heart Valve Leaflet Metabolism Studies a) Heart Valve Leaflet Viability Testing Tissue viability will be assessed by measurement of $^3$H-glycine or $^3$H-proline incorporation into trichloroacetic acid (TCA) precipitable proteins (50). Leaflets will be placed in polystyrene tubes containing 12 μCi of tritiated substrate in μl of DMEM supplemented with 15 μg/ml ascorbic acid. Samples will be incubated at 37° C. for 48 hr in a 5% $CO_2$ atmosphere. Tissues will be washed four times with phosphate-buffered saline, dehydrated with ethanol, washed with ether, and weighed. Tissues will be rehydrated with 200 μl of water, and then solubilized by addition of 1M NaOH, incubation at 60° C. for 1 hr, and sonication twice for 20 sec each. Homogenates will be centrifuged at a 12,000 xg for 5 min, and 100 pl aliquots for the supernatants will be placed on Fisher GFC glass fiber discs. The filter discs will be dried and proteins precipitated by addition of 10% TCA for 30 min followed by five ethanol and two ether rinses, and drying. Discs will be placed in 10 ml of Cytoscint scintillation fluid and tritium incorporation will be measured by scintillation spectrometry. This approach permits estimation of total proteins accumulated in the intra- and extracellular spaces of the leaflet, but does not account for any proteins which might not be incorporated into the extracellular matrix of the issues, i.e., released into the medium prior to cross-linking. Clarification of whether there is significant synthesis of proteins not localized in the extracellular matrix would provide a more complete picture of overall protein synthesis in this tissue. Additionally, this approach does not clarify the distribution of synthesis between collagen and non-collagen proteins, this will be evaluated as described below.

b) Collagen Biosynthesis

Weighted tissue fragments will be incubated at 37° C. in serum free Dulbecco's modified Eagle's medium containing 5 μCi/Ml L-[2, 3-$^3$]proline and supplemented with 50 μg/ml ascorbic acid for optimal collagen biosynthesis and 50 μg/ml μ-aminopropionitrile to retard cross-linking (51). the medium will be separated from the tissue, and phenylmethylsulfonyl fluoride (0.5 mM), EDTA 20 mM), and N-ethylmaleimide (10 mM) will be added to inhibit proteolysis. The tissue will then be washed three times with ice-cold phosphate buffered saline and extracted with 0.5M acetic acid plus 1 μg/ml pepstatin and 10 mM N-ethylmaleimde. The extracts will be further dialyzed against acetic acid and clarified by centrifugation; medium samples will also be dialyzed against acetic acid. After precipitation ion 10% TCA, the recovered proteins will be dissolved in 0.05M NaOH and an aliquot removed for total $^3$H-proline incorporation. Relative collagen synthesis will then be assayed by measuring the radioactivity that remains TAC-soluble after limited digestion with bacterial collagenase. This enzyme will be purified to remove non-specific protease activity by Sepharose S-300 column chromatography according to Peterkosfy and Diegelmann (52). Samples will be incubated with or without collagenase ( approx. 25 units) plus 10 mM N-ethylmaleimide for 5 hr at 37° C. bovine serum albumin (50 μg/ml) will be added to the extract as carrier protein; trichloroacetic acid will be added to a final concentration of 10% and tannic acid to 0.025%, and the mixture kept at 4° C. for 60 min. Precipitated proteins will be collected by centrifugation (5,000 xg for 5 min) and washed three times in 5% TCA. The relative rate of collagen synthesis to noncollagen synthesis will be calculated after counting the radioactivity in both fractions and multiplication of the noncollagen protein radioactivity by 5.4 to correct for the relative abundance of imino acids in collagen (22.2%) versus noncollagen proteins (4.1%) (53).

C) Oualitative analysis of collagens (collagen typing)

Interrupted gel electrophoresis, as described by Sykes, et al. (54) will resolve type I, III, and V collagen, the main subtypes found in leaflets. After radiolabeling with $^3$H-proline, the tissue will be electrophoresed on nonreducing 5% SDS polyacrylamide gel in the presence of 0.05M urea until the dye front has migrated approximately ⅓ of the total run distance. Then 20 μl of β-mercaptoethanol will be added to each well. Since type III collagen is disulfide bonded, its migration is retarded relative to the α chains of type I and V collagen until the reducing agent is added. Therefore, the α1(III) chain can be resolved from the α1 (I) chain. The α1(V) and α2(V) chains migrate between the α1(I) and the α1(III) chains. The gel will be soaked in 10 volumes of sodium salicylate (pH6.0) for 30 min to enhance $^3$H emission intensity 955) and exposed to Kodak SB X-ray film for fluorography. The ratio of type III to type I collagen will be determined by scanning densitometry.

d) Cyanogen Bromide Isolation of Elastin from Collagen in Tissues

Separation of elastin and collagen is based on the fact that elastin contains no methionine and so resists digestion by cyanogen bromide. Leaflet pieces will be treated with 50 mg/ml cyanogen bromide in 70% formic acid under nitrogen for 24 hr at room temperature. The extract is removed and residual material washed five times with water at 90° C. the extract and washes contain collagen and other solubilized proteins. The insoluble residue is taken as elastin. This material can be solubilized by multiple extractions with 0.25M oxalic acid at 98° C. The extracts will be dialyzed against water at 4° C. to prevent coacervation.

e) Glvcosaminoglycans

Tissue will be labelled in culture medium with 10 μCi/ml [6-$^3$H] glucoasime (specific activity 30 Ci/mmole) for 24 hr at 37° C. After labeling the issue will be washed five times to remove unincorporated label, lyophilized, and extracted with 1M acetic acid. The samples will be precipitated with 20% trichloroacetic acid, and radioactivity measured by liquid scintillation spectrometry.

3. Molecular Biology Techniques a) Nucleic acid cloning cDNA probes for type I collagen chains, type III collagen, type IV collagen chains, and elastin will be subcloned into transcribable vectors (pGEM4Z or pGEM7Z, according to requirements for particular restriction endonuclease sites in the polycloning sites). These constructs can be used to transform competent E. coli (56) which are replicated in large-scale cultures to generate additional plasmid and inserts.

The constructs to be used are:

| LOCUS (INSERT) | VECTOR | CLONING SITE I | CLONING SITE II |
|---|---|---|---|
| COL1A1 (Hf677) | pGEM7Z | EcoR1 | EcoR1 |
| COL1A2 (Hf32) | pGEM7Z | EcoR1 | AaII |
| COL4A1 (pE123) | pGEM4Z | EcoR1 | EcoR1 |
| COL4A2 (pE18) | pGEM4Z | EcoR1 | HindIII |
| COL3A1 (Hf934) | pGEM4Z | EcoR1 | HindIII |
| HDE-3 (elastin) | pGEM4Z | EcoR1 (+T7 = antisense) | SacI (+Sp6 = sense) |

For ligation of DNA to a cloning vector both the insert DNA and the plasmid (5 µg of each) will be digested with appropriate restriction enzymes to produce complimentary termini. The DNAs will be precipitated to remove extraneous proteins and salts. When a single enzyme is used, the plasmid is dephosphorylated with calf intestinal alkaline phosphatase (CIAP) in the presence of 1 mM $ZnCl_2$ to remove $5^1$-phosphate groups and prevent recircularization during litigation CIAP-treated plasmids will be repurified, or else they will affect ligation and transformation efficiency (57). the insert and vector DNAS are mixed in molar ratios of 1:1, 1:3, and 3:1 and reacted with T4 ligase at 4° C. overnight (58). The JM109 strain of E. coli will be used for all transformations and is purchased from Promega as competent cells. Aliquots of the ligation mixtures containing up to 50 ng of cloned DNA will be mixed with cells, chilled on ice for 10 min, and then heat shocked at 42° C. for 50 sec. The transformed cells will be allowed to proliferate without selection antibiotic for 1 hr and will then be streaked onto antibiotic-containing (50 µg/ml ampicillin) Luria-Bertani (LB) medium plates. After overnight incubation, single cell colonies will be picked and grown overnight in LB medium containing ampicillin. DNA is isolated by the SDS-NaOH lysis (59), digested with appropriate restriction endonucleases, and electrophoresed on 1% agarose gels containing 0.089M Tris; 0.089M borate and 0.002M EDTA (IX TBE) to UV-light visualize insert DNA after ethidium bromide staining.

Large scale preparations of plasmid DNA will be prepared from positive clones by twice expanding bacteria volume 100-fold in overnight incubations in the presence of antibiotic. the bacteria will be recovered by centrifugation, washed in pH 8.0 buffer and frozen at –80° C. to aid lysis. the bacteria will be treated successively with 20% sucrose in 50 mM Tris-Cl, pH 8.0; 10 mg/ml lysozyme in water, and 0.25M EDTA, pH 8.0 to limit nuclease activity, and then lysed in 2% Triton X-100, 40 mMTris-Cl, pH 8.0 and 60 mMEDTA. the lysates will be cleared of debris by centrifugation for 45 min at 15,000 xg. Plasmid DNA is separated from chromosomal DNA and RNA protein by equilibrium centrifugation (48 hr at 15,000 xg) in cesium chloride at a density of 1.386 g/ml and ethidium bromide at 0.74 mg/ml. The closed circular plasmid DNA bands at a higher density than nicked circular or linear DNA, or protein. After removal from the tube, ethidium bromide is extracted by multiple n-butanol washes, and the DNA dialyzed to remove CsCl. After digestion of RNA with 10 µg/ml RNAase A and proteins with 50 µg/ml proteinase K, plasmid DNA is precipitated from 0.3M sodium acetate with 70% ethanol. (59).

b) Nucleic Acid Labeling

DNA or RNA probes will be non-radioactively labeled with digoxigenin-II-UTP, a sterol not found in biological materials, thus reducing background staining (60). After excision and purification of the cDNA from the construct, labeled double stranded DNAs will be prepared by the random priming reaction using the Klenow fragment of DNA polymerase (61). Labeled RNA probes will be synthesized by in vitro transcription of DNA. Both the pGEM4Z and pGEM7Z plasmids contain SP6 and T7 RNA polymerase promoters flanking opposite ends of the multiple cloning site. By linearizing the plasmid at the end of the insert opposite from the selected polymerase promoter, antisense or sense RNA probes can be prepared depending upon orientation of the insert and the RNA polymerase used.

The α1(I) collagen and α1(IV) collagen probes both have 5' and 3' EcoRI ends and so could be cloned in either direction. Before being used for in situ hybridization as riboprobes, the directions of insertion will be analyzed according to restriction endonuclease digestion and mapping of the fragments.

Assessment of Collagen and Elastin mRNA i. in situ hybridization

In situ hybridization will be used to assess gene function as the technique permits detection of a specific mRNA in a heterogeneous cell population; therefore functional vs. nonfunctional cells can be differentiated. the probes are to be labeled with digoxigenin so that non-radioactive detection can be used. This permits more rapid analysis, eliminates health hazards of radioactivity and permits more detailed detection of the site of hybridization.

Under RNAase-free conditions, 5–10, µm thick cryosections of liquid nitrogen frozen leaflets will be mounted on silane subbed slides (62). Fixation in 4% paraformaldehyde is used to preserve morphology and improve retention without cross-linking proteins thereby making cell ectoplasm impermeable (63). As it will be used here, hybridization is detected with an alkaline phosphatase conjugate. the high alkaline phosphatase activity of fibroblasts (64) will be inhibited by washing the sections in 0.2M HCl to reduce potential background (65). The acid treatment can improve signal-to-noise by permeabilization of the fixed proteins and may be augmented by brief digestion with proteinase K (66). When cDNA probes, the sections are also treated with acetic anhydride in triethanolamine buffer to neutralize positive charges and reduce non-specific binding of the probes (67). Prehybridization at 37° C. will be used to block non-specific binding and to equilibrate the sections with buffer. Prehybridization buffer contains: 50% formamide; 0.6M NaCl, 10 mM Tris-Cl, pH 7.5; 0.02% each of Ficoll type 400, polyvinylpyrrolidone, and bovine serum albumin; 1 mM EDTA, 0.05% each of salmon sperm dNA and yeast tRNA; and 20 mM β-mercaptoethanol. The prehybrization buffer will be replaced with hybridization buffer which will contain, in addition to the above components, 10% dextran sulfate and prove at 2–100 fmol/µl. Both cDNA and RNA probes will be used to establish conditions of optimal detection of MRNA. After hybridization, the sections will be washed with buffers of increasing stringency (decreasing salt concentration and increasing temperature). Eghbali, et al. have reported an extensive washing process for in situ detection of collagen mRNAs in rat hears (68). With RNA probes, RNAase digestion is used to demonstrate specific binding RNAase digestion before hybridization with cDNA probes is used for the same purpose). To detect bound probe specimens will be treated with non-fat dry milk to block non-specific antibody binding, reacted with the rabbit anti-digoxigenin serum, and developed with X-phosphate/NBT substrate for alkaline phosphatase.

Experiments with in situ hybridization include: 1. detection of distribution of collagen and elastin mRNAs in normal leaflet tissue as well as in the myocardial band and the aortic conduit; 2. examination of expression of these same messenger RNAs by cultured fibroblasts; and 3. examination of expression in fibroblasts in repopulated porcine heart valves.

ii. Northern blotting

Total RNA will be isolated from dermal fibroblasts in culture and flow-conditioned repopulated tissues using a modification of the SDS lysis/acid phenol technique of Stalcup and Washington (69) which has been used by the P.I. to isolate hepatocyte RNA in high yield (70). RNA will be separated by electrophoresis on 1.2% formaldehyde agarose gels, blotted onto charged nylon hybridized with $\alpha1(I)$ collagen, $\alpha2(I)$ collagen, type III collagen, $\alpha1(IV)$ collagen, $\alpha2(IV)$collagen, or elastin cDNAs labeled with digoxigenin-II-UTP, and washed under high stringency to obtain specificity of hybridization. The blots will be reacted with an anti-digoxigenin antibody/alkaline phosphatase conjugate and reacted with BCIP/NBT substrate. Relative abundance of MRNAs will be determined with laser densitometry (Emory University). The blots can be decolorized with N,N-dimethyl formamide (55° C.) and stripped of probe with 0.2N NaOH, 0.1% SDS for reprobing.

4. Biomechanical Testing

Tensile tests, performed using a calibrated Instron Model 5565 materials tester and Series IV personal computer interface software and custom-designed specimen clamps require the following sequential tasks:

cut leaflet from valve punch leaflet into "dog bone" shaped specimens circumferential or radial)

measure specimen thickness with a low-mass conductivity device mount and precondition specimen to 300 to 150 kPa (circumferential or radial, respectively)

test load versus elongation specimen to 300 or 150 kPa (circumferential or radial, respectively)

test load versus elongation and plot stress versus strain curves test and plot stress-relaxation curves test and plot ultimate failure curve to provide estimates of ultimate tensile strength, high modulus, and extensibility.

The effect of load on tissue extensibility is depicted in stress versus strain curves where strain is calculated as the change in length compared to fully relaxed tissue, and the measured load is converted to stress by normalizing to load-bearing cross-sectional area.

E. BIBLIOGRAPHY

1. Schneider, P J and Deck, J D, Cardioavas. Res. 15:181–189, 1981.
2. Deck, J D, Thubrikar, M J, Schneider, P J and Nolan, S P, Cardiovasc. Res. 22:7–16, 1988.
3. Reinhart, W H, Experientia 50:87–93, 1994.
4. Carosi, J A and McIntire, L V, Eur. Respir.Rev. 3:598–608, 1993.
5. Owens, G K Physiol. Rev. 75:487–517, 1995.
6. Patrick, C W, Jr. and McIntire, L V, Blood Purif 13:112–124, 1995.
7. Ley, K and Tedder, T F, J. Immunol. 155:525–528, 1995.
8. Ando, J, Tsuboi, H, Korenaga, R, Takada, Y, Toyama-sorimachi, N. Miyaska, M and Kamiya, A, Am. J. Physiol. Cell Physiol, 267:C679–C687, 1994.
9. Davies, P F, Physiol. Rev. 75:519–560, 1995.
10. Willems, IEMG, Havnith, M G, smits, J F M and Daemen, M J A P, Lab. Invest. 71:127–133, 1994.
11. Butt, R P, Laurent, G J and Bishop, J E, Ann. N.Y. Acad. Sci. 752:387–393, 1995.
12. Wiklund, L. Nilsson, B, Berggren, H and Nilsson, F. Scand. J. Thor. Cardiovasc. Surg. 29:1–6, 1995.
13. Kim, Y-J, Bonassar, L J and Grodzinsky, A J, J. Biomechanics 28:1055–1066, 1995.
14. Mauch, C, Hatamochi, A, Scharffetter, K. and Krieg, T., Exp. Cell Res. 178:493–503, 1988.
15. Kolodney, M S and Wysolmerski, R B, J. Cell Biol. 117:73–82, 1992.
16. Tomasek, J J, Haaksma, C J, Eddy, R J and Vaughan, M B, Anatom. Rec. 232–359–368, 1992.
17. Nishiyama, T. Tsunenaga, M, Nakayama, Y, Adachi, E and Hayashi, T, Matrix 9:193–199, 1989.
18. He, Y and Grinnell, F, J. Cell Biol. 126:457–464, 1994.
19. Yamato, M, Adachi, E, Yamamoto, K and Hayashi, T, J. Biochem. Eng. 21:289–305, 1993.
20. Huang, D. Chang, T R, Aggarwa, A, Lee, R C and Ehrlich, H P, Ann. Biomed. Eng. 21:289–305, 1993.
21. Moeller, H D, Bosch, U and Decker, B, J. Anat. 187:161–167, 1995.
22. Bajpai, P. Biocompatibility of tissue analogs, vol. 1, edited by William, D.f CRC Press, Inc. Boca Raton: 1985, p. 5–25.
23. Armiger, L C, Gavin, J B and Barratt-Boyes, B G, Pathology 15:67–73, 1983.
24. Kamiya, A. and togawa, t. Am. J. Physiol. 239:H14-H21, 1980.
25. Fry, DL, Circ. Res. 22:165–197, 1968.
26. Evans, E. Berk, D and Leung, A, Biophys. J. 59:838–848, 1991.
27. Delobel, J. Yang, J, Offerman, M K and Zhu, C, Adv. Bioeng. 22:391–394, 1992.
28. Hammer, D A and Lauffenberger, D A, Biophys. J. 52:475–487, 1987.
29. St. Louis, J. corcoran, P. Rajan, S. Conte, J. Wolfinbarger, L. Hu, J. Lange, PL, Wang, Y N, Hilbert, S L, Analouei, A and Hopkins, R A, Eur. J. Cardiothorac. Surg. 5:458–465, 1991.
30. Domkowski, P W, Messier, R H, Jr. Crescenzo, D G, Alay, H S, Abd-Elfattach, A S, Elbert, S L, Wallace, R B and Hopkins, R A, Ann. Thorac. Surg. 55:413–419, 1993.
31. Mochtar, B, van der Kamp, AWM, Roza-de Jongh, EJM and Nauta, J. Cardiovasc. Res. 18:497–501, 1984.
32. McGregor, CGA, Bradley, J F, McGee J O and Wheatley, D J, Cardiovasc. Res. 10:389–393, 1976.
33. Yoganathan, A P, Eberhardt, C E and Walker, P G. J. Heart Valve Dis. 3:571–580, 1994.
34. Westerhof, N. Elzinga, G and sipkema, P. J. appi. Physiol. 31:776–781, 1971.
35. Walker, P G, Kim, T Y, Muralidharan, E, Miyajima, Y, Delatore, J and Yoganathan, A P, Echocardiography 11:11–28, 1994.

36. Yoganathan, A P, Woo, Y R and Sung, H W, J. Biomechanics 19:433–442, 1986.
37. Fontaine, A A, Ellis, J T, Hopmeyer, J and Yoganathan, A P, ASAIO J. 1995 (In Press)
38. Dell'Orbo, C, De Luca, G, Quacci, D and Soldi, C, Histol. Histopathol. 10:583–588, 1995.
39. Spray, T L and Roberts, W C, Am. J. Cardiol. 40:319–330, 1977.
40. Messier, R H, Jr., Bass, B L, Alay, H M, Jones, J L, Domkowski, P W, Wallace, R B and Hopkins, R A, J. Surg. Res. 57:1–21, 1994.
41. Torii, S. Bashey, R I and Nakao, K, Biochim. Biophys. Acta 101:285–291, 1965.
42. Lester, W. Rosenthal, a. Granton, B and Gotlief, A I, Lab. Invest. 59:710–719, 1988.
43. Grabowski, E F and Lam, F P, Thromb. Haemost. 74:123–128, 1995.
44. Hammer, D A, Tempelman, L A and Apte, S M, Blood Cells 19:261–277, 1993.
45. Koveker, G B, Burkel, W E, Graham, L M, Wakefield, T W and Stanley, J C, J. Vasc. Surg. 7:600–605, 1988.
46. Wechezak, A R, Coan, D E, Viggers, R F and Sauvage, L R, Am. J. Physiol. Heart Circ. Physiol. 264:H520–H525, 1993.
47. Ott, M J and Ballermann, B J, Surgery 117:334–339, 1995.
48. Gosselin, C. Ren, D, Ellinger, J and Greisler, H P, Am. J. Surg. 170:126–130, 1995.
49. Nagel, T. Resnick, N, Atkinson, W J, Dewey, C F, Jr. and Gimbrone, M A, Jr. J. Clin. Invest. 94:885–891, 1994.
50. McNally, R T and Brockbank, K G M, J. Med. Eng. Tech. 16:34–38, 1992.
51. Werb, Z, Tremble, P and Damsky, C H, Cell Differentiation and Development 32:299–306, 1990.
52. Peterkofsky, B and Diegelmann, R, Biochem. 10988–994, 1971.
53. Buckley,, A, Hill, K E and Davidson, J M, Methods Enzymol. 163:674–694, 1988.
54. Sykes, B, Puddle, M, Francis, M and Smith, R, Biochem. Biophys. Res. Commun. 72:1472–1484, 1976.
55. Chamberlain, J P, Anal. Biochem. 98:132–137, 1979.
56. Promega Protocols and Applications Guide. 2nd Edition. Promega Corporation, Madison: 1991, pp. 51–57.
57. Perbal, B. A practical guide t omolecular cloning. 2nd edition. John Wiley and Sons, 1988, pp. 403–405.
58. Birnboim, H C, Methods Enzymol. 100:243–255, 1983.
59. Molecular cloning. A laboratory manual, edited by Sambrook, J., Fritsch, E. F. and Maniatis, T. Cold Spring Harbor Laboratory Press, Cold Spring Harbor: 1989, p. 1.33–1.52.
60. Arnold, N Seibl, R, Kessler, C and Wienberg, J, Biotech. Histochem. 67:57–67, 1992.
61. Feinberg, A P and Vogelstein, B, Anal. Biochem. 137:266–267, 1984.
62. Signer, R H, Lawrence, J B and Villnave, C, BioTech. 4:230–249, 1986.
63. Wilcox, J N, J. Histochem. Cytochem. 41:1725–1733, 1993.
64. Fedde, K N, Cole, D E and Whyte, M P, Am. J. Hum. Genet. 47:776–783, 1990.
65. Lum, J B, BioTech. 4:32–39, 1986.
66. Guiot, Y and Rahier, J, Histochem. J. 27:60–68, 1995.
67. Hayashi, S, Gillam, I C, Delaney, A D and Tener, G M, J. Histochem. Cytochem. 36:677–679, 1978.
68. Eghbali, M, Blumenfeld, O O, Seifter, S, Buttrick, P M, Leinwand, L A, Robinson, T F, Zern, M and Giambrone, M, J. Mol. Cell Cardiol. 21:103–113, 1989.
69. Stalcup, M R and Washington, L D, J. Biol. Chem. 258:2802–2810, 1983.
70. Goldstein, S, Sertich, G. Phillips, L S and LeVan, K R, Molec. Endo. 2:1093–1100, 1988.

What is claimed is:

1. An apparatus for subjecting implant heart tissue to a physiologic pulsatile flow, comprising:

a piston-type pump;

a flexible elastomeric bladder containing a fluid that is mounted inside of a fluid-filled chamber, the pump serving to displace the fluid within the chamber so as to simulate a pulsatile flow within the bladder and to shield the fluid within the bladder from contamination by the pump, wherein the fluid within the bladder is a blood-analog suitable for providing living cells in heart tissue with nutrients;

a fluid conduit leading from the bladder to a test section adapted to contain at least one aortic valve sample containing living cells;

a fluid conduit leading from the test section to a downstream compliance and resistance element;

a gas exchanger in communication with the blood-analog fluid for providing the at least one aortic valve with proper levels of gases;

a heat exchanger in thermal communication with the blood-analog fluid; and a fluid conduit leading from the compliance and resistance element to the bladder;

wherein the apparatus provides pulsatile flows from a range of pressure regimes and fluid flow regimes.

2. An apparatus as set forth in claim 1, wherein the apparatus provides pulsatile flows having physiologic systolic and diastolic pressures.

3. An apparatus as is set forth in claim 1, further comprising a waveform generator for controlling the piston pump.

4. A bioreactor for studying the effects of physical inputs to heart valve leaflet biochemical functions, comprising:

a pump;

a flexible elastomeric bladder containing a fluid that is mounted inside of a fluid-filled chamber, the pump serving to displace the fluid within the chamber so as to simulate a pulsatile flow within the bladder and to shield the fluid within the bladder from contamination by the pump, wherein the fluid within the bladder is a blood-analog suitable for providing living cells in valvular heart tissue with nutrients for a period of time sufficient to study the mechanical effect of physiologic pumping on live cells;

a fluid conduit leading from the bladder to a test section adapted to contain natural aortic valve samples mounted in parallel;

a fluid conduit leading from the test section to a downstream compliance and resistance element;

a gas exchanger in communication with the blood-analog fluid for providing the natural aortic valves with the proper levels of gases;

a heat exchanger in thermal communication with the blood-analog fluid; and a fluid conduit leading from the compliance and resistance element to the bladder;

wherein the apparatus provides pulsatile flows from a range of pressure regimes and fluid flow regimes to the heart valves so that the effect of such regimes on cells within the heart valves can be studied.

5. An apparatus as set forth in claim 4, wherein the apparatus provides pulsatile flows having physiologic systolic and diastolic pressures.

* * * * *